United States Patent
Busiashvili (10) Patent No.: US 11,607,508 B1
(45) Date of Patent: Mar. 21, 2023

(54) DEVICE FOR SUBLINGUAL APPLICATION OF A THERAPEUTIC DOSE OF MEDICATION IN FRACTIONS

(71) Applicant: Stat Capsule Inc., Glendale, CA (US)

(72) Inventor: Yuri Busiashvili, Pacific Palisades, CA (US)

(73) Assignee: Stat Capsule Inc., Glendale, CA (US)

(*) Notice: Subject to any disclaimer, the term of this patent is extended or adjusted under 35 U.S.C. 154(b) by 0 days.

(21) Appl. No.: 17/317,164

(22) Filed: May 11, 2021

Related U.S. Application Data (60) Provisional application No. 63/129,770, filed on Dec. 23, 2020.

(51) Int. Cl.
*A61M 15/00* (2006.01)
*B05B 11/00* (2023.01)
*A61M 11/00* (2006.01)

(52) U.S. Cl.
CPC ........ *A61M 15/003* (2014.02); *A61M 11/006* (2014.02); *A61M 15/009* (2013.01); *B05B 11/0081* (2013.01); *B05B 11/0083* (2013.01)

(58) Field of Classification Search
CPC .... A61M 15/003–0041; A61M 15/009; A61M 15/0056; A61M 15/0058; B05B 7/04–0491
See application file for complete search history.

(56) References Cited

U.S. PATENT DOCUMENTS

| | | | |
|---|---|---|---|
| 3,260,464 A * | 7/1966 | Harant | B05B 7/30 239/375 |
| 4,137,914 A | 2/1979 | Wetterlin | |
| 4,886,495 A * | 12/1989 | Reynolds | A61M 5/284 604/416 |
| 5,171,219 A * | 12/1992 | Fujioka | B05B 11/02 604/82 |
| 5,456,677 A | 10/1995 | Spector | |

(Continued)

FOREIGN PATENT DOCUMENTS

| | | | |
|---|---|---|---|
| CN | 2432936 Y * | 5/2001 | A61J 3/00 |
| EP | 1260209 A2 | 11/2002 | |

(Continued)

OTHER PUBLICATIONS

English translation for JP 2004000579, translated on Jul. 13, 2022 and translated through Search engine through clarivate analytics.*

(Continued)

*Primary Examiner* — Tu A Vo
(74) *Attorney, Agent, or Firm* — Ralph D Chabot (57) ABSTRACT

A sublingual type medication delivery device includes a container body having a predetermined volume of solvent with a spray dispenser attached at one end of the container and at the opposite end of the container is a housing which contains medication to be discharged into the container and mixed with the solvent to form a diluted medication for fractional delivery of the medication over a period of time. The housing can either be a tablet crusher for introducing medicament in solid form into the container or the housing can be a capsule having liquid medicament that is delivered through a needle that pierces the capsule wall.

4 Claims, 6 Drawing Sheets

(56) References Cited

U.S. PATENT DOCUMENTS

| | | | | |
|---|---|---|---|---|
| 5,692,644 | A * | 12/1997 | Gueret | B05B 11/0083 |
| | | | | 222/129 |
| 5,752,505 | A * | 5/1998 | Ohki | A61M 15/0028 |
| | | | | 128/203.15 |
| 6,474,861 | B1 * | 11/2002 | De Laforcade | B65D 81/3211 |
| | | | | 215/DIG. 8 |
| 6,655,525 | B2 * | 12/2003 | Song | B65D 81/3211 |
| | | | | 215/DIG. 8 |
| 6,869,419 | B2 | 3/2005 | Dragan et al. | |
| 7,185,648 | B1 * | 3/2007 | Rand | B01F 31/65 |
| | | | | 128/200.23 |
| 7,452,350 | B2 | 11/2008 | Yeakley | |
| 7,658,721 | B2 | 2/2010 | Steiner et al. | |
| 8,342,370 | B2 | 1/2013 | Ross et al. | |
| 8,376,988 | B2 | 2/2013 | Perovitch | |
| 9,861,578 | B1 | 1/2018 | Busiashvili | |
| 10,188,585 | B1 | 1/2019 | Busiashvili | |
| 2004/0195276 | A1 * | 10/2004 | Fuchs | B05B 11/02 |
| | | | | 222/386 |
| 2005/0247729 | A1 * | 11/2005 | Durant | A01G 25/145 |
| | | | | 222/129 |
| 2007/0036858 | A1 | 2/2007 | Schneider | |
| 2011/0067576 | A1 * | 3/2011 | White | A47J 27/2105 |
| | | | | 99/323.1 |
| 2012/0288602 | A1 * | 11/2012 | Diatlo | A23L 2/04 |
| | | | | 99/506 |
| 2013/0284824 | A1 * | 10/2013 | Morikis | B05B 1/3405 |
| | | | | 514/642 |
| 2018/0029864 | A1 * | 2/2018 | Blackburn | B05B 9/047 |
| 2018/0093287 | A1 * | 4/2018 | Dhir | B05B 11/3008 |
| 2018/0263852 | A1 | 9/2018 | Aiken et al. | |
| 2020/0071055 | A1 * | 3/2020 | Pidoux | A45D 34/04 |
| 2020/0398005 | A1 * | 12/2020 | Simpson | A61M 11/007 |

FOREIGN PATENT DOCUMENTS

| | | | |
|---|---|---|---|
| GB | 2480856 | 12/2011 | |
| JP | 2004000579 A * | 1/2004 | B05B 3/0463 |
| JP | 2004290669 A * | 10/2004 | |

OTHER PUBLICATIONS

English translation for JP 2004290669, translated on Jul. 12, 2022, translated by Espacenet.com.*

English translation for CN 2432936, translated by Search Clarivate analytics, translated on Dec. 27, 2022.*

* cited by examiner

DEVICE FOR SUBLINGUAL APPLICATION OF A THERAPEUTIC DOSE OF MEDICATION IN FRACTIONS

CLAIM OF PRIORITY

Priority is herewith claimed under 35 U.S.C. § 119(e) from Provisional Patent Application No. 63/129,770, filed Dec. 23, 2020. The disclosure of this Provisional Patent Application is incorporated by reference herein in its entirety.

BACKGROUND OF THE INVENTION

The fastest way to deliver medication to the bloodstream noninvasively is sublingual, because of the rich venous network under the tongue. Nitroglycerin is given sublingually since its absorption is very rapid and for that reason is not always safe. Another medication that is used for angina control, Nifedipine is manufactured as an incapsulated liquid taken orally for gastro-intestinal absorption. When a capsule with Nifedipine dissolves in the stomach, Nifedipine is absorbed all at once and may cause serious complications and even death.

Nitroglycerin (hereafter, "NTG") and Nifedipine are associated with many undesirable side effects, when given in a single sublingual dose in cardiac emergency.

In most medical emergencies outside a medical facility, a person usually has a choice of taking a pill or capsule or call for treatment by paramedics. The time before the help arrives or the ingested medication begins to be absorbed is usually at least 20-30 minutes—which is too long a time period, especially when the patient's condition is critical and exhibits symptoms such as chest pain, hypertensive crisis, with blood pressure over 200, paroxysmal tachycardia rapid atrial fibrillation flutter with heart rate over 120 bpm, myoclonic seizures with aura that often precede generalized tonic clonic seizures with loss of consciousness etc.

When NTG is given as a sublingual tablet or as a spray to control chest pain as quickly as possible, a full dose is usually absorbed in its totality at once and its absorption may be delayed if the patient is experiencing dry mouth. A single liquid dose delivered with a multi-dose sprayer can not be divided into fractions, because a multi-dose sprayer is operating on the principle: one spray—one therapeutic dose. As a result, undesirable hemodynamic effects often follow, resulting in syncope, hospital admission and extended stay.

Rate of blood absorption is how quickly a medication is absorbed into the bloodstream. Safety is dose related and how fast a single therapeutic dose is absorbed into the bloodstream. The faster the full dose is absorbed to achieve maximal therapeutic benefit, the more likely that undesirable side effects of the single therapeutic dose will occur.

A typical multi dose sprayer will contain 60 or 200 doses in a single bottle. The multi dose sprayer has the following negative characteristics:

First, an anxious patient may administer more than one dose and develop serious side effects. Hemodynamic effects, such as drop of blood pressure, heart rate, syncope are dose related. Second, a single dose is volume dependent and the dose can vary by more than 50%, between when administering the first few dosages when the sprayer is full, compared to when the sprayer is less than half full or only a few dosages remain in the bottle.

From a hygiene standpoint, especially with the concern regarding virus spread such as COVID-19, multi dose, multi patient use in the hospital increases the potential for transfer of droplet viral infection from one person to another.

The person with a sudden onset of paroxysmal tachycardia, rapid fibrillation-flutter, usually takes medication in a tablet form and paramedics are called. Sublingual therapy of paroxysmal tachyarrhythmia does not exist. Either way, at least 20-30 minutes will pass until a tablet taken orally will be absorbed into the bloodstream or the treatment is administered by medical personnel.

Antiarrhythmic drug application to the nasal mucosa, in the hospital setting, even though approved by FDA, is still experimental and not popular.

Liquid capsular Nifedipine can be used sublingually, but not approved for sublingual use by FDA because of the frequent dose related side effects, when taken orally and absorbed in its totality.

Some tablets are easier dissolved than others. Amiodarone, which is routinely used for treatment of rapid paroxysmal atrial fibrillation, is given over an extended period of time intravenously in the hospital setting—a bolus of 300 mg is given as a drip over ½ hour to be continued as a drip at a slower rate.

When an Amiodarone tablet is dissolved for sublingual drip use to be self-administered, it quickly precipitates to the bottom of the single dose sprayer and the sprayer bottle needs to be repeatedly shaken every minute for half an hour prior to each timed next spray of a fraction of the full therapeutic dose.

Alternatively, the remaining portion of a single dose tablet or another 200 mg tablet is swallowed for delayed action by at least 20-30 minutes—which is the time required for gastro-intestinal (hereafter, "GI") absorption. The same principle applies to a capsular liquid medication: part of it is delivered to a predetermined solvent volume, and the residual medication that remains in a capsule, can be swallowed with the capsule for GI absorption.

SUMMARY OF THE INVENTION

Disclosed is a device for sublingual administration of NTG or other medications provided in either a dry form, such as a powder or tablet; or provided in an incapsulated liquid form. The device is used to deliver up to a single therapeutic dose of medication(s) by dilution of the medication(s) into a liquid solution thereby allowing fractional doses to be administered over a period of time rather than administering the entire therapeutic dose as a bolus.

Because some patients can not handle the physical effects of a prescribed therapeutic dose as a bolus, the disclosed device allows for the therapeutic dose to be gradually administered over time and, if the patient's condition and vital signs permit, to be discontinued prior to complete administration of the therapeutic dose. The patient's vital signs can be monitored by various third party products commercially available. This methodology ensures rapid absorption of heart medication but at lower concentration, which reduces the risk of a severe drop in blood pressure which could lead to syncope. The medication solution is designed to be sublingually administered in a medical emergency, typically by the patient who is sensing the onset of a cardiovascular condition.

By way of example, if the therapeutic dose of NTG is a dose of 300 mcg in liquid form, the method includes adding a solvent or diluent for dilution to increase the overall volume containing NTG and thereafter administer the diluted medication. The quantity of diluent used will be that volume required for sublingual administration of a therapeutic dosage which is preferably between 1 cc-5 cc. The diluted solution containing the medication is administered in volume fractions sublingually and repetitively, as a spray, preferably over given time intervals. Continuous assessment of the user's vital signs, such as blood pressure and heart rate, are made possible using portable monitoring such as, for example, wrist worn medical devices.

In another embodiment, the assessment and delivery of medication can be done with dissolution of the medication in a dry powder or tablet form in a predetermined volume of solvent or diluent. As with the liquid NTG medication described in the preceding paragraph, dilution enables the volume of the solvent to equate with an entirely dissolved tablet. Then a fraction of a dose NTG in mcg can be equated with the fraction of the solvent volume in which a minimal therapeutic single dose NTG is dissolved. For example, if 400 mcg tablet is dissolved in 2 cc of a solvent, then when ½ cc of a solution delivered sublingually means that 100 mcg NTG is delivered in this volume. This fractional dosage is a fraction of a therapeutic dose and is much less likely to result in dose related unwanted side effects as opposed to a sudden absorption of a whole therapeutic dose in its totality.

As used herein, the term "therapeutic dosage" means the single dosage prescribed by a physician for the patient to treat a cardiac event. The dosage will be in milligrams and can either be in a dry tablet form or a liquid in a capsule form.

The term "fractional portion" means the portion of the prescribed therapeutic dosage which is contained in a single sublingual application.

The term "pre-determined period of time" refers to the time delay between sublingual applications. This term will be provided by the patient's physician.

The medical device serves two purposes. First, a patient can not overdose on the medication since the container only contains 1 prescribed therapeutic dosage. Second, sublingual administration of fractionated portions, delivers the medication to a patient's bloodstream over a period of time rather than all at once as is the case of a bolus; thereby reducing the risk that a patient will experience a severe drop in blood pressure and will not experience syncope.

In a preferred embodiment, the medical device comprises:

a cylindrical container having two ends with respective apertures, each of the ends adapted for threadable engagement;

a predetermined volume of solvent disposed within the container;

a spray dispenser threadably engaged to the first end of the container; and, a medication delivery means attached to the second end of the container.

Preferably, one or both of the apertures may be covered with a protective film to prevent solvent contamination. The protective film would be removed or punctured prior to the medication being combined with the solvent.

The medications for delivery by fractionated dosage may come in an anhydrous form such as a tablet or in a liquid capsular form. In order to fractionate the dosage to perform the invention, the medication must first be solubilized with the diluent in the container. Thus, a means for medication delivery into the container is required. If the medication is in the form of a fast dissolving tablet, the means is depositing the tablet into the container with no further action necessary. However, if the medication tablet is not fast dissolving, the means would be a tablet crusher which is temporarily attached to the container to create more surface area for the medication to be solubilized in the diluent.

Alternatively, if the medication is in a liquid capsular form, the means for delivery of medication into the container is a capsule piercing assembly temporarily attached to the container which will provide a flow path to extract the liquid medication from the capsule and into the container.

If a single medication is to be solubilized, the medication delivery means will be threadably attached to the end opposite the end attached to the spray dispenser. If two medications are to be solubilized within the container, in addition to the medication delivery means attached to the end opposite the end of the spray dispenser, a second medication delivery means would be attached, either by removing the first medication delivery means after its medication has been mixed with the container solvent, or by temporarily removing the spray dispenser and attaching the second medication delivery means in its place. Following its medication being mixed with the container solvent, the second medication delivery means can be detached and the spray dispenser attached.

Optionally, the medical device further comprises a vibration unit operably attached to the container for either assisting with mixing the medication with the solvent or solubilizing any precipitates back into solution.

The medication delivery means can be a mechanism for delivery of dry medication which would require crushing a pill or tablet into smaller pieces to be more easily solubilized by the container solvent. The medication delivery means can also be a mechanism for delivery of liquid medication, for example, from a capsule containing liquid medication. Depending on the patient's needs, one or more medication delivery means can be used for delivering medication into the container for solubilization.

In the case of solid medication, the delivery means is a device for crushing a tablet of medication to increase the surface area of the medicament prior to mixing with the solvent. The tablet crusher would preferably include a main body threadably attached to the container on one end. The main body would preferably have a recess for insertion of the tablet or pill. At the other end, a threadable cap would engage female threads present on the sides of the recess and the cap would crush the tablet as the cap is rotated relative to the main body.

In the case of liquid medication in a liquid capsular form, the medication delivery means is preferably a capsule loader with a needle to pierce the capsule containing the liquid medication.

A vibration unit can be operationally attached to the container. In a preferred embodiment, the vibration unit has a tip which is press-fit into attachment with a sleeve that is sized to snugly fit about the outer circumference of the medication delivery means which in turn is attached to the container. In this way, the vibration unit can be operatively attached to the container housing to assist with mixing medicament and solvent as well as to maintain the medicament in solution and prevent precipitation.

In order to break down a single therapeutic dose in a form of a tablet, or incapsulated liquid, into fractions, for safety and availability considerations, the dose is diluted with a pre-determined volume of solvent. Once the medication(s) has been solubilized into the solution, the full volume of a solvent will contain a single therapeutic dose of a medication(s). Once diluted in the solvent, it is thereafter possible to sublingually deliver medicament to a patient in volumetric fractions of a single therapeutic dose using the spray dispenser. A predetermined spray volume will correlate with a fraction of a single therapeutic dose of a dissolved tablet and or incapsulated liquid.

It is to be understood that the device can be used for combining different medications. By way of example, a single therapeutic dose of NTG can be diluted into the solvent using the tablet crushed as the medication delivery means and Nifedipine can be diluted into the solvent using the capsule loader as the medication delivery means. For the second medicament to be diluted within the container, either the first medication delivery means must be unthreaded from engagement to the base of the container, or it remains in place and the sprayer is temporarily detached from the container and the second medication delivery means is temporarily attached.

The solvent container, or sprayer bottle, can be calibrated with volumetric scale divisions on the side, like a syringe (½ cc divisions), which corresponds to a fraction dose of dissolved medication. For example, if 400 mcg of nitroglycerin is dissolved in 2 ml of a solvent, then every ½ cc of the liquefied nitroglycerin will contain 100 mcg of nitroglycerin. Thus, it may take more than a single spray to deliver the desired fractional dose.

In the case of using Nifedipine 10 mg in liquid capsule form and Propranolol 10 mg in a tablet form, both are dissolved for example, in a 2 cc solvent. Thus, ½ cc of the solvent-medication solution will contain 2.5 mg of either medication and could be delivered sublingually in volumetric volume fractions at the same time, with continuous monitoring of blood pressure and heart rate.

The capsule loader used for delivery of liquid medication, preferably has a needle on one side, open to air, and a needle hub on the other side, opening into the solvent container. The loader further includes a cap which prevents solvent from escaping when in the threaded closed position.

The tablet crusher has two sections that define a variable inner volume into which a tablet is placed and upon rotating one section relative to the other, the inner volume will be reduced and eventually crush the tablet into smaller pieces of medication. There is a small opening into the solvent container for the crushed pieces to enter.

Because the medical device is designed to administer a single therapeutic dose, the container portion housing the solvent can be disposable after a single use thereby avoiding possible contamination and inadvertent viral transmission.

The medication having been diluted is thereafter administered to a patient in fractionated dosages over predetermined time intervals. However, if the patient is wearing a monitoring device for heart rate and blood pressure, depending on the real-time data, treatment may be discontinued before the therapeutic dose has been completely administered.

Thus, the embodiments described herein can be used in a method for delivering a therapeutic dose of a medication to a patient in fractional portions comprising the steps of:

a) combining a therapeutic dose of at least one medication in a pre-determined volume of solvent to form a medication solution;

b) administering a portion of the medication solution to the sublingual area of a patient when the patient senses the onset of a cardiovascular condition;

c) monitoring the vital signs of the patient;

d) waiting a pre-determined period of time and if the patient's vital signs do not improve, administer an additional portion of the medication solution; and, e) repeating steps c) and d) if the patient's vital signs do not improve or until the medication solution has been completely administered.

DESCRIPTION OF THE PREFERRED EMBODIMENT

Figure 1:
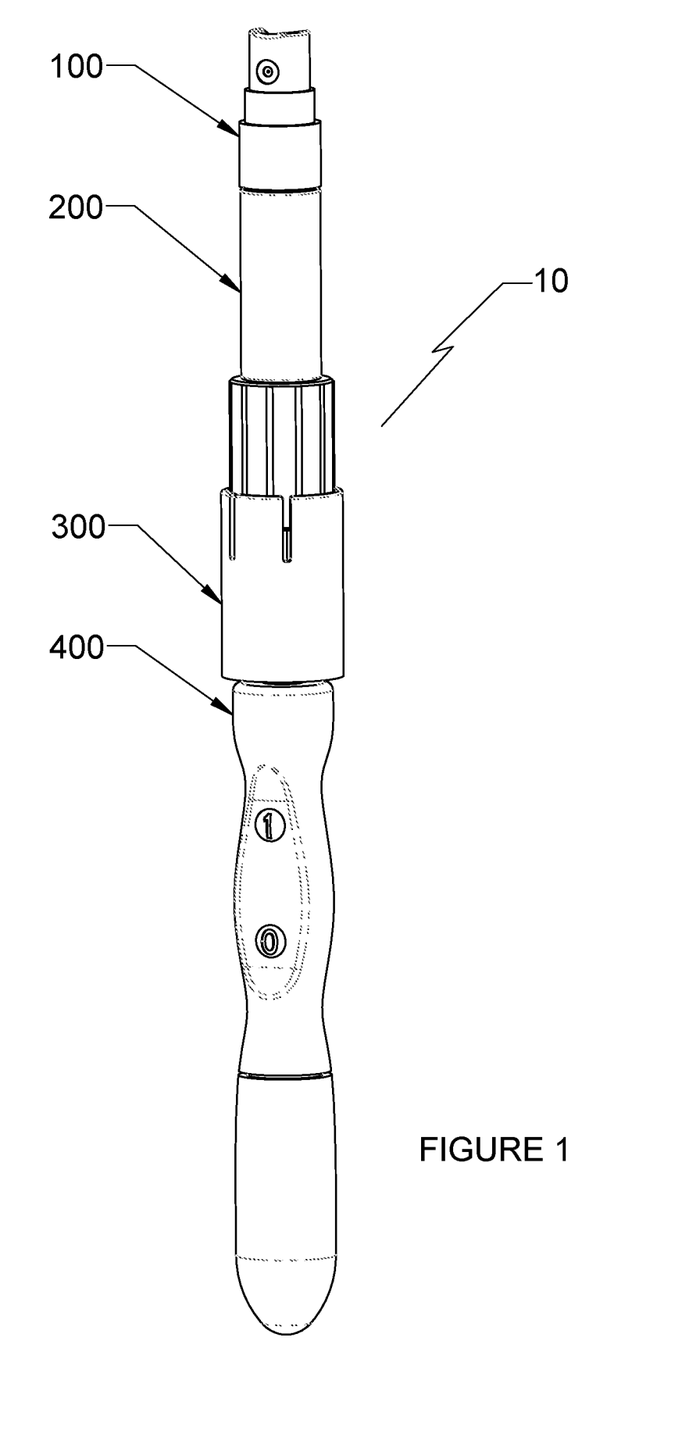
FIG. 1 is a side view of the medical device that includes the vibration unit.
Figure 4:
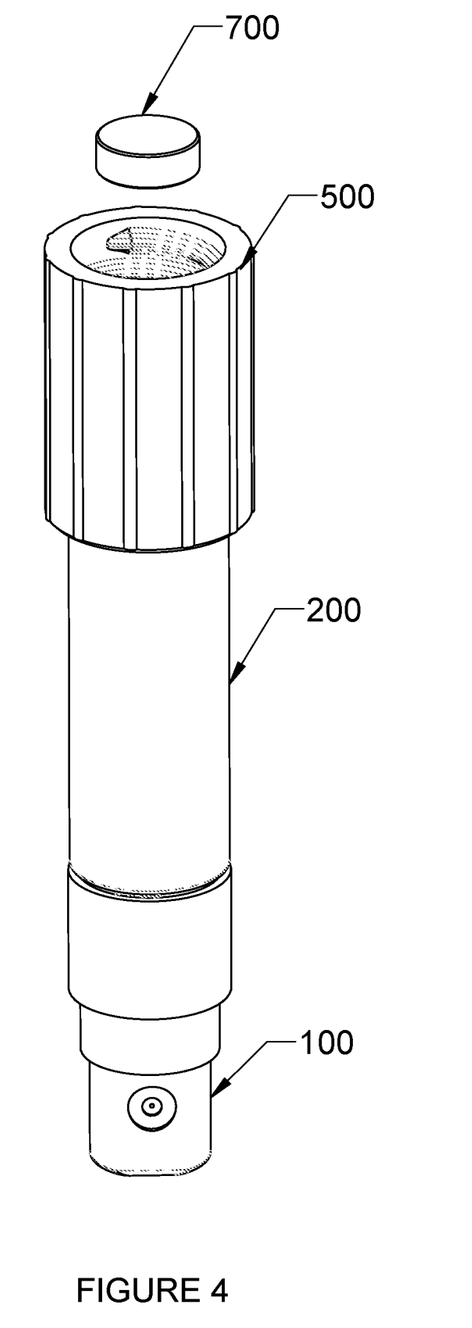
FIG. 4 is a view of the tablet crusher connected as part of the medical device.
Figure 5:
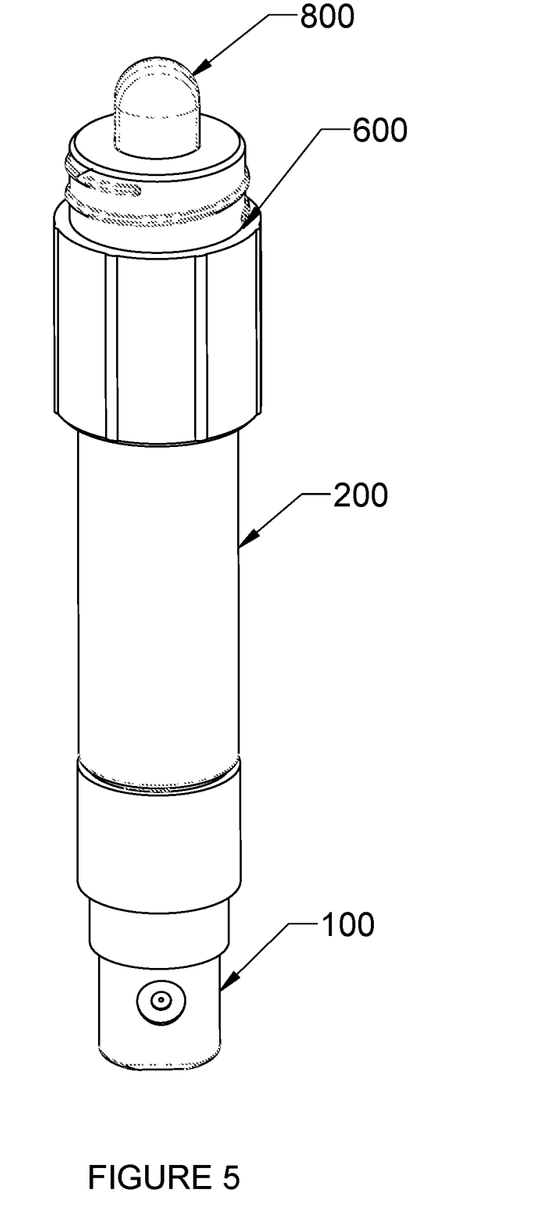
FIG. 5 is a view of the liquid capsule dispenser connected as part of the medical device.
Figure 7:
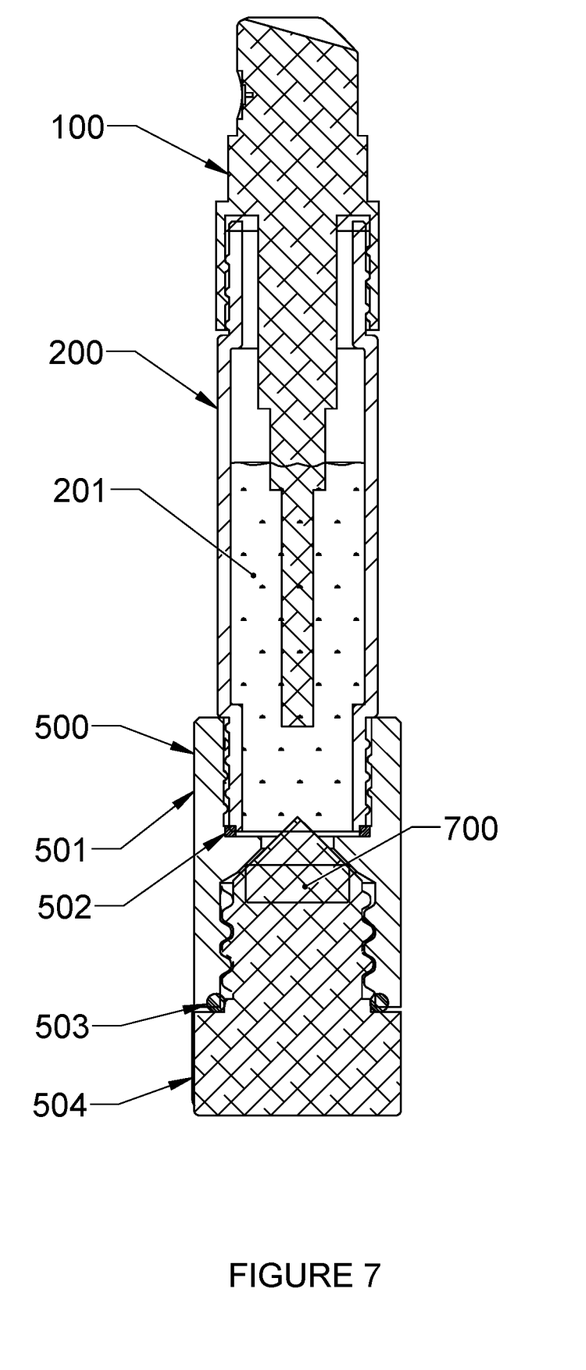
FIG. 7 is a view taken along line 7-7 of FIG. 6.
Figure 9:
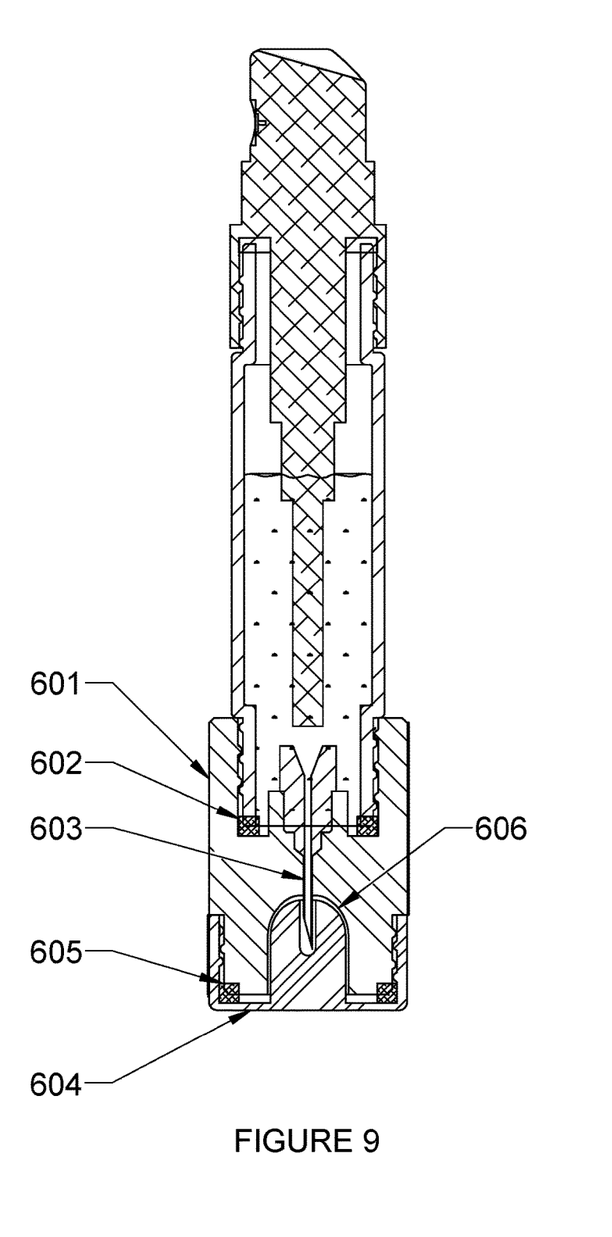

FIG. 1 illustrates medical device 10 and comprises a cylindrical container 200, a spray dispenser 100 operatively attached to one end of the container, a pre-determined amount of solvent 201 within cylindrical container 200; and, a medication delivery means, which is either a tablet crusher assembly 500 shown in FIGS. 4 and 7 or a liquid capsule assembly 600 illustrated in FIGS. 5 and 9. Either assembly is used for introducing medication in tablet 700 or liquid form 800 respectively into cylindrical container 200 for mixing with solvent 201 therein. Preferably, spray dispenser 100 is threadably connected to cylindrical container 200.

As can be viewed in FIGS. 7 and 9, a well-known design is used for spray dispenser 100 which comprises a pump head and inlet tube which extends into solvent 201 and female threads for threadably engaging the threads present on container 200. In addition, cylindrical container 200 includes a first end engaging spray dispenser 100 and a second end engaging a medication delivery means 500 or 600. Cylindrical container 200 has two apertures, one at each respective end of the container.

Optionally, medical device 10 further comprises a vibration unit 400.

The medication delivery means would be for application of medication in solid form 700, in which case the medication delivery means is tablet crusher assembly 500 or for liquid medication contained within a capsule 800, in which case the medication delivery means is capsule loader assembly 600.

Figure 6:
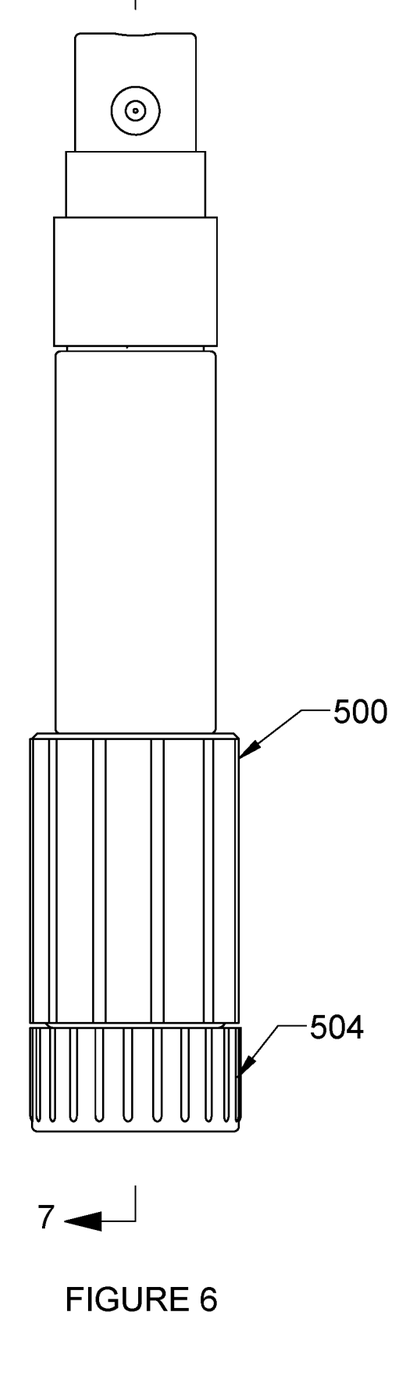
FIG. 6 is a view of the medication delivery means (tablet crusher) connected as part of the medical device.

For use of tablet crusher assembly 500 as the medication delivery means, its purpose is to increase the surface area of the medicament 700 prior to mixing with the solvent 201. FIGS. 4, 6 and 7 best illustrate the positioning of assembly 500 relative to container 200 as well as the operation of the crusher assembly. Tablet crusher assembly 500 comprises a closure 501 for threadable attachment to the lower end of container 200 and gasket 502. Closure 501 further comprises a recess into which tablet 700 can be inserted. The recess includes female threads for threadable attachment to crusher knob 504. An O-ring 503 is present. As crusher knob 504 is rotated, it will contact tablet 700 and crush into smaller pieces which will be small enough to enter an opening to the base of container 200. For ease of viewing, crusher knob 504 is not illustrated in FIG. 4.

Figure 8:
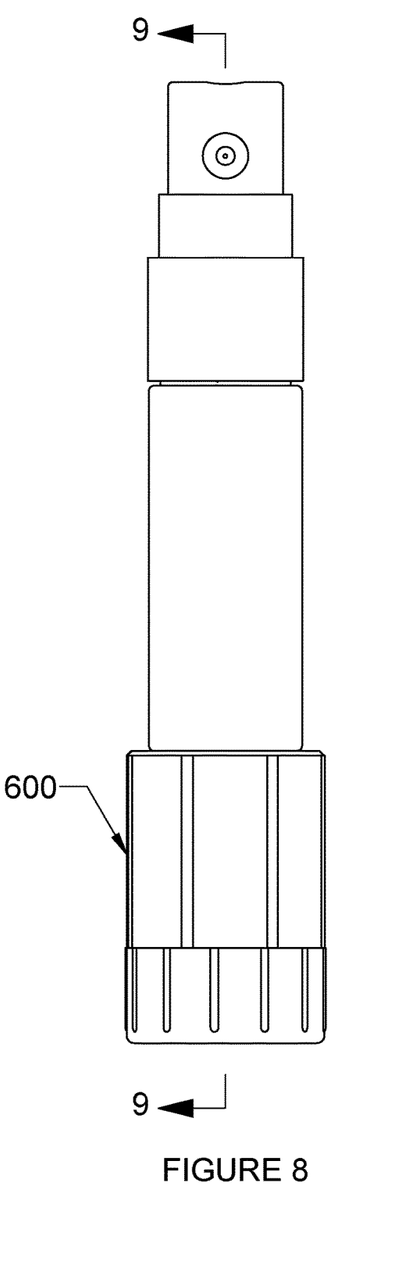
FIG. 8 is a view of the medication delivery means (liquid capsule dispenser) connected as part of the medical device; and, FIG. 9 is a view taken along line 9-9 of FIG. 8.

For use of capsule loader assembly 600 as the medication delivery means, FIGS. 5, 8 and 9 best illustrate the positioning of assembly 600 relative to container 200 as well as the operation of the assembly. Capsule loader assembly 600 comprises a closure 601 for threadable attachment to the lower end of container 200 and gasket 602 as well as a needle 603 which has its tip end extending into a recess 606 sized to receive a liquid capsule 800. The recess includes female threads for threadable attachment to cap 604. A gasket 605 is present. As cap 604 is rotated, it will contact capsule 800 and crush the capsule which forces the liquid medicament through needle 603 into the base of container 200. For ease of viewing, cap 604 is not illustrated in FIG. 5.

Figure 3:
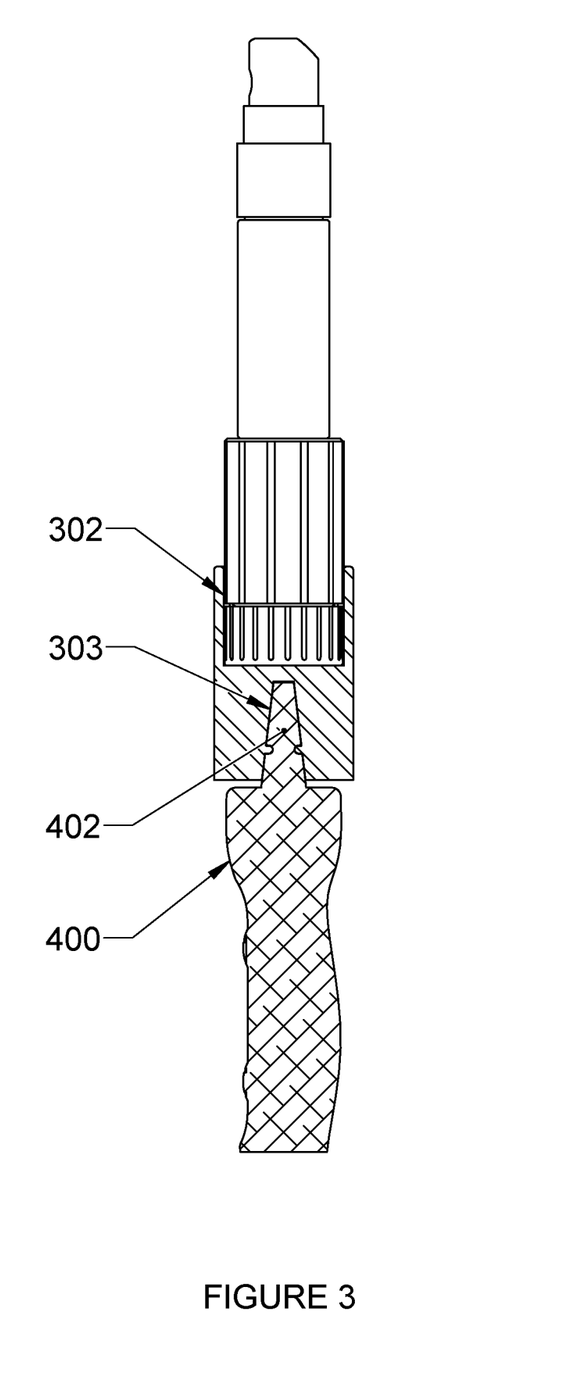
FIG. 3 is a view taken along line 3-3 of FIG. 2.

Once the medication delivery means has been connected to container 200, if the user desires the vibration unit 400 to be incorporated, it is operatively connected to container 200 through the use of a sleeve 300 that has a cavity 302 for snugly receiving the medication delivery means and a spring finger 301 to engage. Vibration unit 400 has a tip 402 which is inserted into socket 303 present in sleeve 300 for attachment as best illustrated in FIG. 3.

Figure 2:
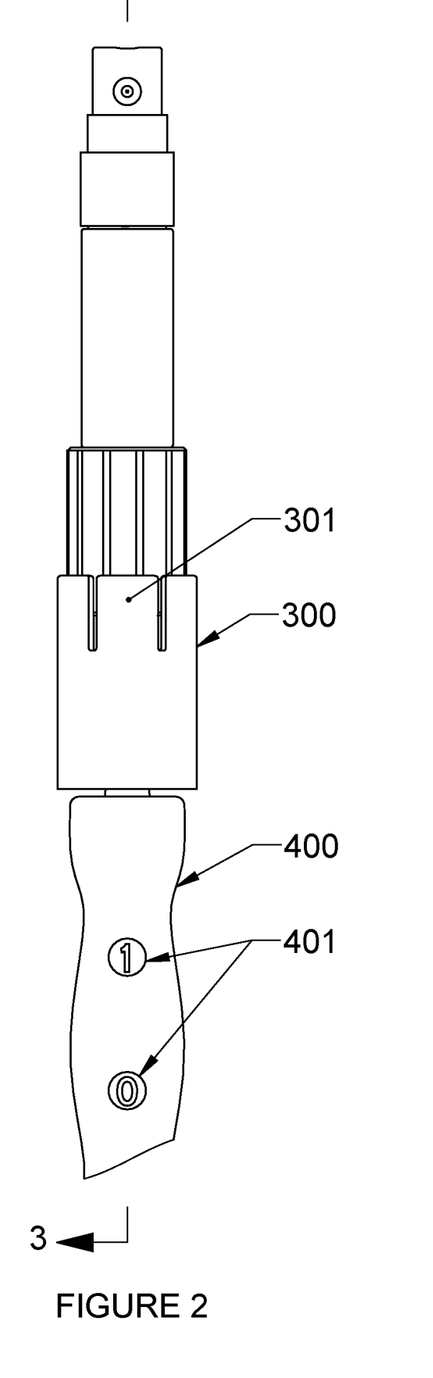
FIG. 2 is an alternate view of the medical device illustrated in FIG. 1.

FIG. 2 illustrates a hand-held battery operated vibration unit 400 which includes power on-off switches 401.

Depending on the medication type, either tablet crusher assembly 500 or capsule loader assembly 600 is used as the medication delivery means.

The selected medication delivery means is thereafter operationally attached to container 200. Container 200 has a sprayer 100 on one end and an aperture on the opposite end by which the medicament present in the medication delivery means can displace and mix with solvent 201 present in container 200.

If desired, vibration unit is operatively connected to container 200.

The medication having been diluted with solvent 201 is then administered to a patient in fractionated dosages over a predetermined time intervals. If the patient is wearing a monitoring device for heart rate and blood pressure, depending on the real-time data, treatment may be discontinued before the therapeutic dose has been completely administered.

Figure 10:
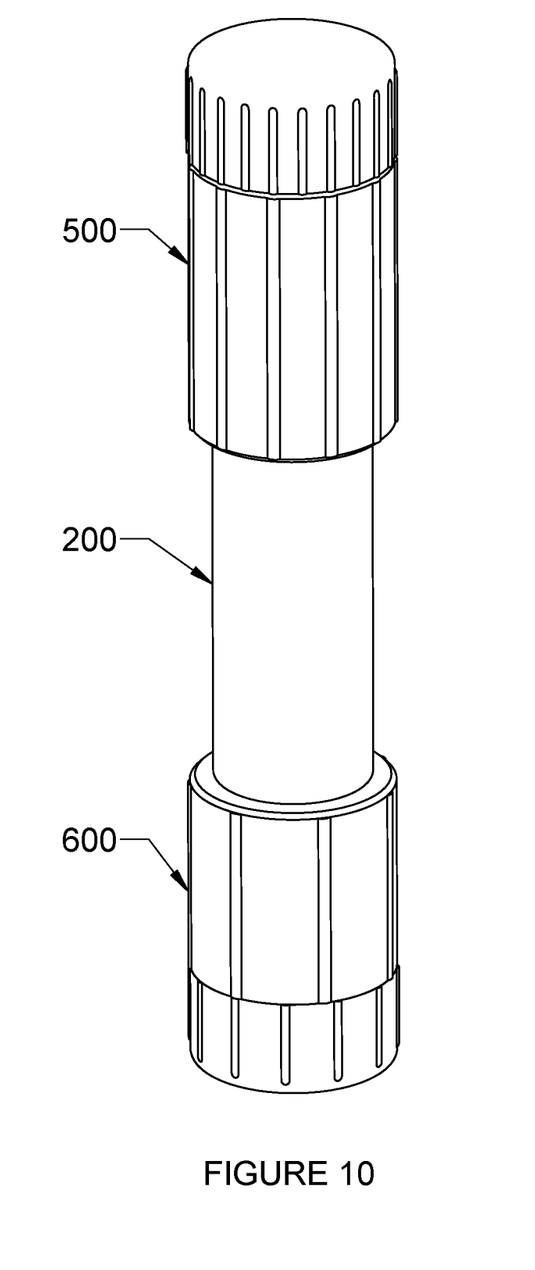
FIG. 10 illustrates an embodiment of different medication delivery means threadably attached to opposing ends of the cylindrical container.

FIG. 10 illustrates an embodiment where a tablet crusher assembly 500 is threadably attached to one end of container 200 and a capsule loader assembly 600 is threadably attached to the opposite end. In this embodiment, separate medications can be delivered and solubilized with solvent 201. Thereafter, either tablet crusher assembly 500 or capsule loader assembly 600 can be removed and pump spray dispenser 100 threadably attached to container 200. Pump spray dispenser 100 will be required to be primed prior to sublingual administration of the medication-solvent solution.

The embodiments of medical device 10 can thus be used as part of a method for delivering a single therapeutic dose of a medication to a patient in fractional portions comprising the steps of:

a) combining a single therapeutic dose of at least one medication in a pre-determined volume of solvent to form a medication solution;

b) administering a portion of the medication solution to the sublingual area of a patient when the patient senses the onset of a cardiovascular condition;

c) monitoring the vital signs of the patient;

d) waiting a pre-determined period of time and if the patient's vital signs do not improve, administer an additional portion of the medication solution; and, e) repeating steps c) and d) if the patient's vital signs do not improve or until the medication solution has been completely administered.

I claim:

1. A medical device comprising:
a container having a first end and a second end, the first end comprising a first aperture, the second end comprising a second aperture, each of the first and second ends adapted for threadable engagement;
a predetermined volume of solvent disposed within the container;
a spray dispenser engaged to the first end of the container;
a tablet crusher having a first end and a second end, the first end of the tablet crusher is located on a side that is opposite of the second end of the tablet crusher, in which the first end of the tablet crusher is attached to the second end of the container, and wherein the tablet crusher comprises a chamber adapted to receive and thereafter crush a single homogeneous tablet of medication for complete mixing with the container solvent;
a hand-held vibrator located external of the container and operably connected to an external surface of the container; and
a sleeve having a first recess adapted to receive an elongated tip of the hand-held vibrator and a second recess adapted to receive the second end of the tablet crusher.

2. A medical device comprising:
a container having a first end comprising a first aperture and a second end comprising a second aperture, each of the first and second ends adapted for threadable engagement;
a predetermined volume of solvent disposed within the container;
a spray dispenser engaged to the first end of the container; and,
a capsule loader having a chamber and needle, the capsule loader having a first end and a second end, and a capsule recess positioned on the second end of the capsule loader configured to receive a capsule, the first end of the capsule loader is located on a side that is opposite from the second end of the capsule loader, in which the first end of the capsule loader is configured to threadably receive the second end of the container, and wherein, the second end of the capsule loader adapted to receive a liquid capsule of medication and thereafter displace the liquid contents of the capsule through an interior of the needle for mixing with the container solvent, wherein the contents of the capsule is configured to travel into a first end of the needle and exit through a second end of the needle, and
a cap, the cap is removably attached to the second end of the capsule loader, the cap comprising a central protrusion that corresponds to the capsule recess and the central protrusion is configured to be received within the capsule recess, the protrusion comprises a hole that is configured to accommodate the first end of the needle.

3. The medical device of claim 2 further comprising a vibrator that is located external of the container and operably connected to an external surface of the container.

4. The medical device of claim 3 further comprising a sleeve having a first recess adapted to receive one end of the vibrator and a second recess adapted to receive the second end of the capsule loader.

* * * * *